(12) United States Patent
Mizunoya et al.

(10) Patent No.: US 6,397,681 B1
(45) Date of Patent: Jun. 4, 2002

(54) PORTABLE ULTRASONIC DETECTOR

(75) Inventors: Hajime Mizunoya; Yoshio Akutsu; Shigenori Aoki; Shigeru Miwa, all of Ibaraki-Ken (JP)

(73) Assignee: Hitachi Construction Machinery Co., Ltd., Tokyo (JP)

( * ) Notice: Subject to any disclaimer, the term of this patent is extended or adjusted under 35 U.S.C. 154(b) by 0 days.

(21) Appl. No.: 09/321,120

(22) Filed: May 27, 1999

(30) Foreign Application Priority Data

May 28, 1998 (JP) .......................................... 10-164207

(51) Int. Cl.[7] .............................................. G01N 29/04
(52) U.S. Cl. ....................................................... 73/620
(58) Field of Search ........................... 73/620, 629, 633

(56) References Cited

U.S. PATENT DOCUMENTS

| | | | | |
|---|---|---|---|---|
| 4,099,416 A | * | 7/1978 | Niklas ......................... | 73/620 |
| 4,304,133 A | * | 12/1981 | Feasmster. III .............. | 73/633 |
| 4,441,369 A | * | 4/1984 | Lessard et al. ............... | 73/620 |

\* cited by examiner

*Primary Examiner*—John E. Chapman
(74) *Attorney, Agent, or Firm*—Mattingly, Stanger & Malur, P.C.

(57) ABSTRACT

This portable ultrasonic detector has a moved distance instrument comprised of an encoder for detecting a moved amount and a counter for counting the moved amount signal outputted from the encoder, as a means for obtaining position information of an ultrasonic probe. When moving the ultrasonic probe on the surface of the object on the occasion of the inspection, the moved distance instrument measures the moved amount of the ultrasonic probe. The measured moved amount of the ultrasonic probe is sent to an arithmetic processing section of the device body. Also, the ultrasonic detector detects A-scope data when scanning the inspected object with the ultrasonic probe, and executes the predetermined processing by using the data. The ultrasonic detector combines the A-scope data and the moved distance data of the ultrasonic probe to make an inner scope image (B-scope image, etc). When repeatedly scanning the same spot of the object with the ultrasonic probe in order to make the B-scope image, etc. and display them on a display section, peaks of defect echo waves are memorized in piles, and further two defect images or more are displayed on the B-scope image. This ultrasonic detector is configured to draw a storage-type B-scope images. Thereby, defect images can be evaluated in detail and a defect position can be detected accurately.

15 Claims, 11 Drawing Sheets

B-SCANNING

PORTABLE ULTRASONIC DETECTOR

BACKGROUND OF THE INVENTION

1. Field of the Invention

The present invention relates to a portable ultrasonic detector, and more particularly, to a portable ultrasonic flaw detector that obtains position information by use of an encoder unit, that is portable and this is capable of accurately detecting defects within an object to be inspected by displaying images showing the inner state of the inspected object based on data for A-scope display and data of the position information.

2. Description of the Related Art

In an ultrasonic detector, an ultrasonic probe is placed on a surface of an object to be inspected and is moved on the surface in a specific direction. The probe emits pulses of ultrasonic waves to the object periodically and receives echoes of the ultrasonic waves returned from the inside of the object in order to detect waveform information of the echoes. The echo waveform information is stored in a waveform memory as digital data. According to the ultrasonic detector, A-scope images showing waveforms such as the echoes of defects and the like are displayed on a screen of a display section by use of the data that is read out from the waveform memory at a suitable timing. Further, inner scope images showing the inside of the object, that is, B-scope images or C-scope images may be indicated on the display screen by combining the A-scope images with moved distance information (position information) of the probe.

Conventional ultrasonic detectors configured so that the B-scope images or the C-scope images can be displayed are mainly of the set-up type. The set-up type ultrasonic detectors have a structure such that the object to be inspected is placed on a sample table of a detector body and the probe supported by a moving mechanism to be opposite to the object is moved so as to scan it. The moving mechanism is provided with a measuring unit for measuring a moved amount of the probe. When making the above-mentioned images, data with regard to the moved amount, which is obtained by the measuring unit, is used.

Also, when detecting defects such as cracks within a welded member and the like, an angle beam method has been generally used. This angle beam method is such that, while moving the probe in the specific direction along the surface of the object, the probe emits the ultrasonic pulses toward the inside of the object in a direction inclined at an angle and detects the reflected echoes returned from the inside of the object. According to the angle beam method, if there is a defect such as a crack in a depth direction or a hollow within the object, both the upper and lower ends of the defect can be detected, and a shape or a type and the like of the defect can be evaluated because the angle beam method makes it possible to evaluate a size of the defect by measuring the size.

While using the conventional portable ultrasonic detector to make the A-scope images, a measurement operator (an inspector) carries it to the spot where the object exists and holds the probe thereof with his hand, and puts and moves it on the surface of the object in a manually operated mode. Since the conventional portable ultrasonic detector cannot detect a moved amount of the probe structurally, it could not display the B-scope images or the images based on the data obtained by the angle beam method. However, it has also been required for the portable ultrasonic detector to be capable of making/displaying B-scope images or the images based on the angle beam method, and further to be capable of simplifying acquisition of the defect echo waveforms by use of the position information of the probe, which is obtained by a measuring unit for measuring the moved amount of the probe, and accurately detecting positions of the defect.

SUMMARY OF THE INVENTION

It is an object of the present invention to provide a portable ultrasonic detector capable of getting echo waveforms of defects simply and improving detection accuracy on positions of the defects by enabling to carry out making/displaying B-scope images or images due to the angle beam method with simple structure.

The portable ultrasonic detector of the present invention has the following structure in order to attain the above-mentioned object.

The portable ultrasonic detector has an instrument comprised of an encoder for detecting a moved amount and a counting section (a counter) for counting the moved amount signal outputted from the encoder, as a means for obtaining position information of an ultrasonic probe. The device body of the detector includes the counting section on its main board. When moving the ultrasonic probe on the surface of the object on the occasion of the inspection, the moved amount of the ultrasonic probe is measured. The measured moved amount of the ultrasonic probe is sent to an arithmetic processing section of the device body. Also, the ultrasonic detector detects A-scope data when scanning the inspected object with the ultrasonic probe, and executes the predetermined processing by using the data.

The aforementioned ultrasonic detector has a structure that combines the A-scope data and the moved distance data of the ultrasonic probe to make an inner scope image (B-scope image and the like). When repeatedly scanning the same spot of the object with the ultrasonic probe in order to make the B-scope image, etc. and display them on a display section, peaks of defect echo waves are stored in memory in groups, and further two defect images or more are displayed on the B-scope image.

In the aforementioned structure, when repeatedly scanning the same spot of the object, concerning the defect echo waves generated on the A-scope on the occasion of each scanning action, the peak is detected and memorized whenever carrying out the scanning action. For example, when drawing the B-scope, two defect images or more are displayed per defect. Thus, the ultrasonic detector is configured to generate storage-type B-scope images on a display screen. Thereby, defect images can be evaluated in detail and the defect position can be detected accurately.

In the aforementioned structure, further, when carrying out an angle beam method, the inner scope image is made and displayed. In the arithmetic processing section, a plurality of A-scope data, which can be obtained when moving the ultrasonic probe in a direction different from the movable direction of the encoder for the scanning action, are stored in groups in a memory thereof. When displaying the images, a display means displays the image showing the inner state of the object by use of the data stored in the arithmetic processing section.

When carrying out the angle beam method for inspecting the defect generally, this inspection is carried out while confirming a depth direction or a width direction by moving the ultrasonic probe repeatedly with a short distance in a direction substantially perpendicular to an actual scanning direction (the movable direction of the encoder). Thus, defect echoes (the A-scope data) obtained when operating the ultrasonic probe repeatedly with the short distance are stored in groups, and thereby two dimensional information is stored (the information concerning the width and depth of the defect), and when the image is displayed, the accurate position and shape of the defect can be detected.

In particular, it is required for the portable ultrasonic detector to carry out the inspection in places with undesirable environment by moving the angle probe (doing the scanning action of the angle probe) bit by bit manually. The environment for the inspection is very poor. In case of such an inspection, it is difficult for an inspector with less experience to get available images, in comparison with the experienced inspector. Therefore, the ultrasonic detector of the present invention is provided with the structure or means for indicating a criteria useful for judging whether the produced images are based on the proper inspection or not, or whether the manual scanning operation of the ultrasonic probe is proper or not.

DESCRIPTION OF THE PREFERRED EMBODIMENTS

Hereinafter, preferred embodiments of the present invention will be described with reference to the accompanying drawings.

Figure 1:
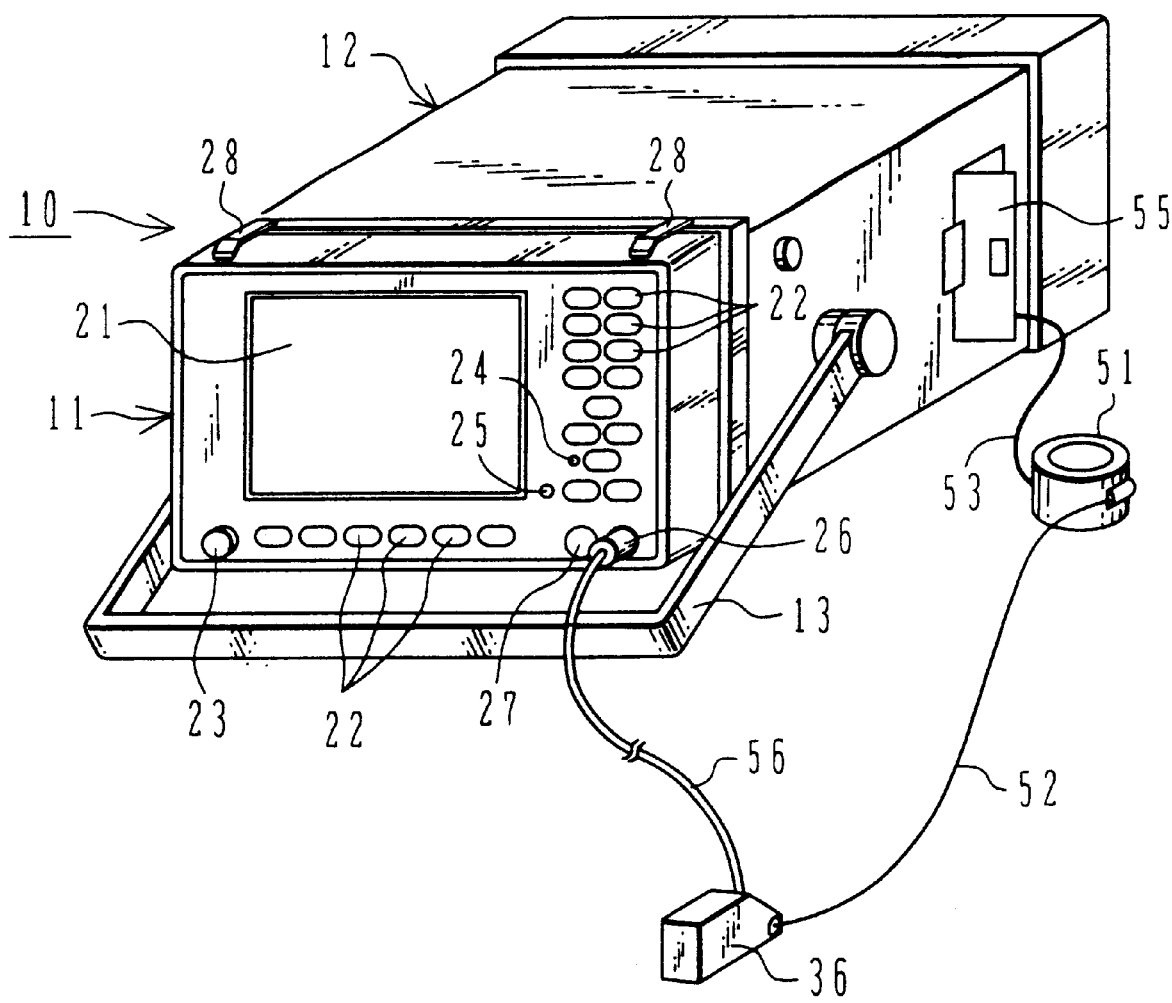
FIG. 1 is a perspective view showing an external appearance of the portable ultrasonic detector of the present invention.

Although this ultrasonic detector is intended for use as a portable device, use of the detector in a set-up style is shown in FIG. 1. As shown in FIG. 1, an ultrasonic (flaw) detector 10 is comprised of a device body 11 for carrying out an inspection by use of ultrasonic waves, and a support casing 12 in which the device body 11 is set.

The support casing 12 is made of metal plates, for example, so as to have a box shape and a predetermined strength necessary for supporting the device body 11. The support casing 12 has an opening at its front part, into which the device body 11 is fit. A handle 13 which is rotatable is arranged between the side walls of the support casing 12. This handle 13 has a function as a support when using the ultrasonic detector as the set-up type.

The device body 11 has a liquid crystal display section 21 in the front section thereof. For example, TFT is used as the liquid crystal for the display section 21, and the TFT is preferably an elongated color screen which is long from side to side. The display section 21 displays echo waves and the like which are obtained on the basis of measurement. In the peripheral region of the display section 21, a plurality of various command operating keys 22 which are used on the occasion of the measurement, a power source switch 23, a buzzer 24, a LED 25, an input terminal 26, and an output terminal 27 and the like are arranged. Suspended sections 28 used for fitting up a carrying band to the device body 11 are arranged at two spots on both sides of the upper section of the device body 11.

Figure 2:
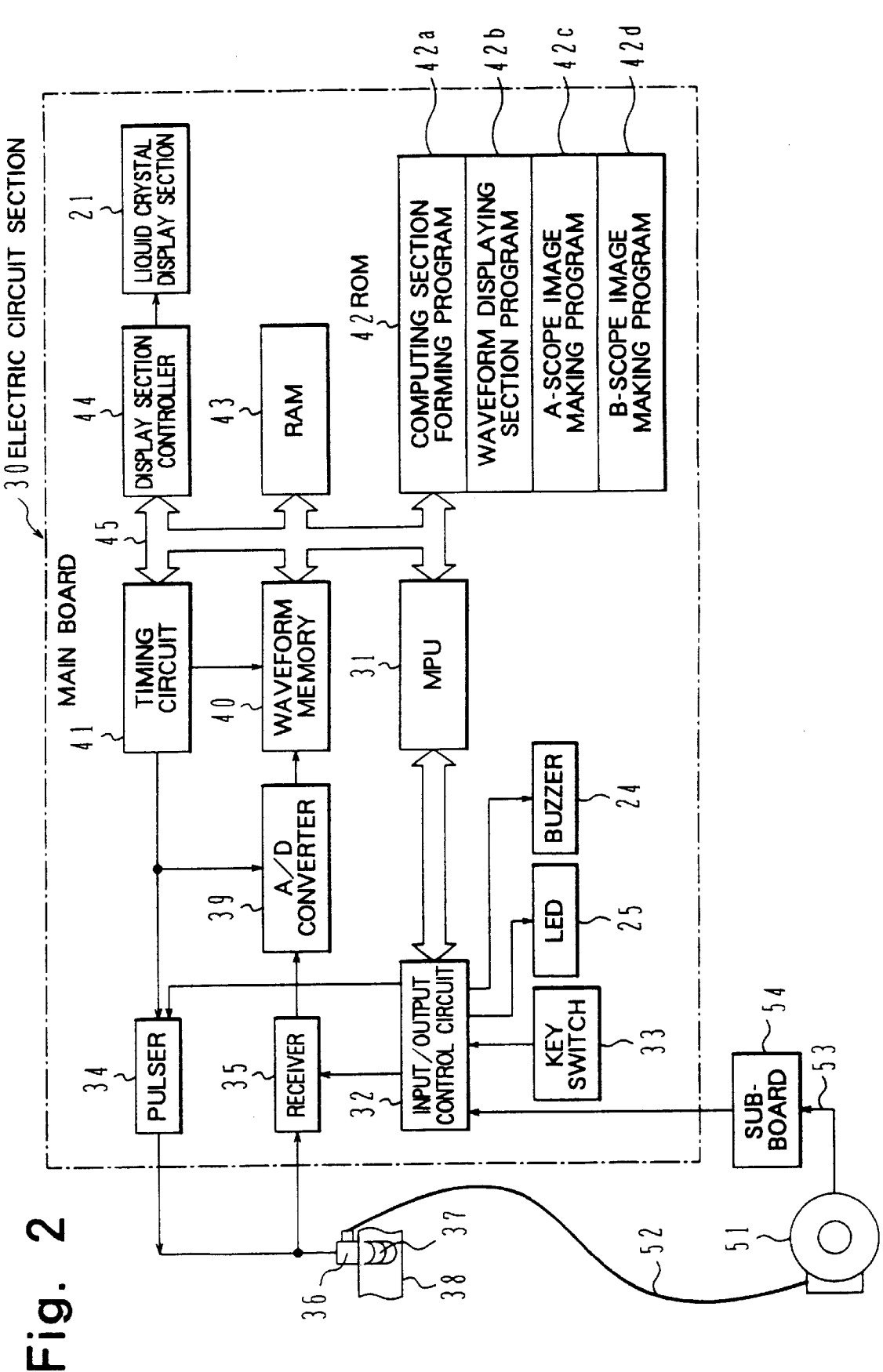
FIG. 2 is a block diagram showing a system configuration of the ultrasonic detector.

The above-mentioned device body 11 has a main board built-in. An electric circuit section for executing various control and signal processing for ultrasonic measurement (ultrasonic flaw inspection) is arranged on the main board. FIG. 2 shows a system configuration of the electric circuit section 30. This electric circuit section 30 includes a MPU (arithmetic processing section) 31 for executing control of sending/receiving ultrasonic waves, computing/processing measured data, and control of the contents displayed on the screen of the display section 21. An input/output control circuit 32 is arranged between the MPU 31 and each of input and output sections of the electric circuit section 30. The input/output control circuit 32 controls the input and output sections based on the commands of the MPU 31. The input section includes a key switch 33. This key switch 33 corresponds to each of the above-mentioned various operating keys 23 and in a practical manner several key switches are provided for the electric circuit sections 30. Also, the output section includes a pulser 34, a receiver 35, and further the above-mentioned LED 25 and buzzer 24.

Ultrasonic emission signals outputted from the input/output control circuit 32 are transmitted to the pulser 34 and further the pulser outputs pulse signals to an ultrasonic probe 36. The probe 36 includes a piezoelectric element and transforms the pulse signal into an ultrasonic wave 37 by the piezoelectric converting operation thereof. By the way, as the ultrasonic probe, there are two sorts of probes, that is, one is a probe (normal incidence probe) for an inspection by a normal beam method and the other is a probe (angle probe) for an inspection by a angle beam method. The probe 36 is the normal incidence probe in this embodiment. When there is a defect within an object 38 to be inspected or measured, it generates a reflected wave based on the ultrasonic wave 37, or a defect echo ultrasonic wave, which returns to the probe 36. The probe 36 receives the defect echo ultrasonic wave. This defect echo ultrasonic wave is transformed into an electric echo signal by the probe 36. The echo signal is transmitted to the receiver 35. In the receiver 35 a gain level and the like is set by control signals from the input/output control circuit 32. The echo signal (waveform signal) inputted through the receiver 35, which is an analog signal, is transformed into a digital signal by an A/D (Analog/Digital) converter 39 and stored in a waveform memory 40.

Various operating signals (commands) inputted through the plural key switches 33 according to the operation of the operating keys are given to the input/output control circuit 32. The various commands on the measurement are inputted into the MPU 31 through the input/output control circuit 32 on the basis of ON/OFF action of the various key switches 33. The contents instructed by the plural key switches 33 are, for example, setting of gains, positioning of pulses or gates, width of the gates, enlargement (zoom) of waveforms and the like. Further, the input/output control circuit 32 actuates the LED 25 or the buzzer 24 to provide necessary messages for a measurement operator (an inspector).

The MPU 31 which executes the computing/processing of the measured data, The aforementioned waveform memory 40, a timing circuit 41, a ROM 42, a RAM 43 and a display section controller 44 are connected to the MPU 31 through a bus 45. The timing circuit 41 adjusts the operating time among an output operation of the pulser 34, a converting operation of the A/D converter 39 and a storing operation of the waveform memory 40. The ROM 42 stores some programs for forming various functional sections in the MPU 31. In the present embodiment, the ROM 42 stores a program 42a for forming a computing section (computing a defect depth and the like), a program 42b for forming a waveform displaying part, a program 42c for making A-scope images, and a program 42d for making B-scope images, etc. The MPU 31 reads out the programs stored in the ROM 42 and realizes necessary functions. For example, the MPU 31 forms the waveform displaying part on the display section 21 by execution of the program 42b, and makes image signals and control signals based on the processing of the measured waveform data stored in the waveform memory 40 and transmits them to the display section controller 44 via the RAM 43 by execution of the programs 42a and 42c. The display section controller 44 controls the contents displayed on the screen of the display section 21 on the basis the image signals and the like, that is, signals used for displaying the images. Thus, the display section 21 displays the A-scope images. Further, the display section 21 displays the B-scope images similarly by execution of the program 42d. When performing the display of B-scope images, this ultrasonic detector utilizes the position information of the probe 36 which is obtained by a probe-moved-distance instrument explained below.

Next, the instrument for obtaining the moved distance information of the probe used for making/displaying the B-scope images will be explained. As shown in FIG. 1, the ultrasonic detector 10 of this embodiment is provided with an encoder 51. This encoder 51 has a wire 52 with a winding structure. When pulling out the wire 52 from the encoder 51, which is normally kept wound up, the encoder 51 outputs electric pulses (moved amount signal) in proportion to the pull-out amount of the wire 52. Accordingly, the pull-out amount of the wire 52 can be measured by counting the number of the pulses outputted from the encoder 51 by means of a counter (counting section). The probe-moved-distance instrument is comprised of the encoder 51, the wire 52, and the counter. In general, the counter is integrated into the MPU 31, for example.

An output line 53 of the encoder 51 is connected to a connection terminal of a sub-board 54 (shown in FIG. 2) arranged within the support casing 12. The sub-board 54 is placed in the vicinity of a side wall of the support casing 12 and the connection with the connection terminal of the sub-board 54 becomes possible when opening a cover section 55 formed in the side wall. As shown in FIG. 2, the sub-board has a connection with the MPU 31 through the input/output control circuit 32. The MPU 31 has a counting function (the counter for the encoder) and gets the information on the pull-out amount of the wire 52 by counting the number of the pulses given from the encoder 51 by means of the counting function.

On the other hand, as shown in FIGS. 1 and 2, the tip of the wire 52 is connected to the probe 36. The probe 36 is electrically connected to the input terminal 26 on the front section of the device body 11 through a cable 56, and further is kept in a state of enabling a scanning operation for inspecting defects within the object 38.

In the above-mentioned structure, when the measurement operator holds the probe 36 and carries out the scanning operation toward a specific direction (a drawing line) on the object 38 with the probe 36, the inner information of the object 38 is obtained by use of the ultrasonic reflected echoes. In addition, the moved distance of the probe 36 is measured by counting the pulses, which are outputted from the encoder 51 in proportion to the moved amount of the probe 36 as mentioned above, by means of the counter for the encoder 51 within the MPU 31, since the wire 52 is pulled out from the encoder 51 in a stretched state so that the pull-out amount thereof is proportional to the moved amount of the probe 36.

Figure 4:
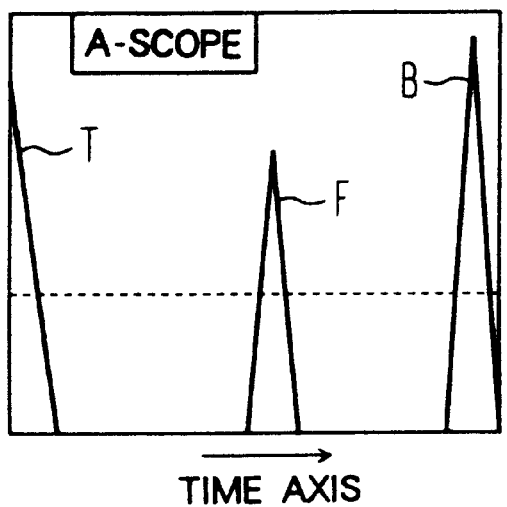
FIG. 4 is a diagram showing one example of an A-scope image.

The ultrasonic detector 10 with the aforementioned structure indicates an A-scope image on its display section, as shown in FIG. 4, which is produced by processing signals on the ultrasonic echo returned from the inside of the object 38. The echo signals are obtained by the probe 36 and the ultrasonic defect detecting function of the ultrasonic detector 10. In FIG. 4, "T" designates a waveform of a transmitting (sending) wave, "F" designates a waveform of a defect (flaw) echo wave, and "B" designates a waveform of a bottom echo wave. Further, since the moved distance data of the probe 36 (the position information of the probe 36) can be obtained through the encoder 51 when the probe 36 is moved for the scanning operation, the combination of the moved distance data and the data of the A-scope image makes it possible to make the B-scope image and display it on the display section. To get the position information of the probe by means of the encoder 51 effectively enables the display of the B-scope image, to confirm the inner state of the object, and to measure a length of the defect and the like.

Figure 5:
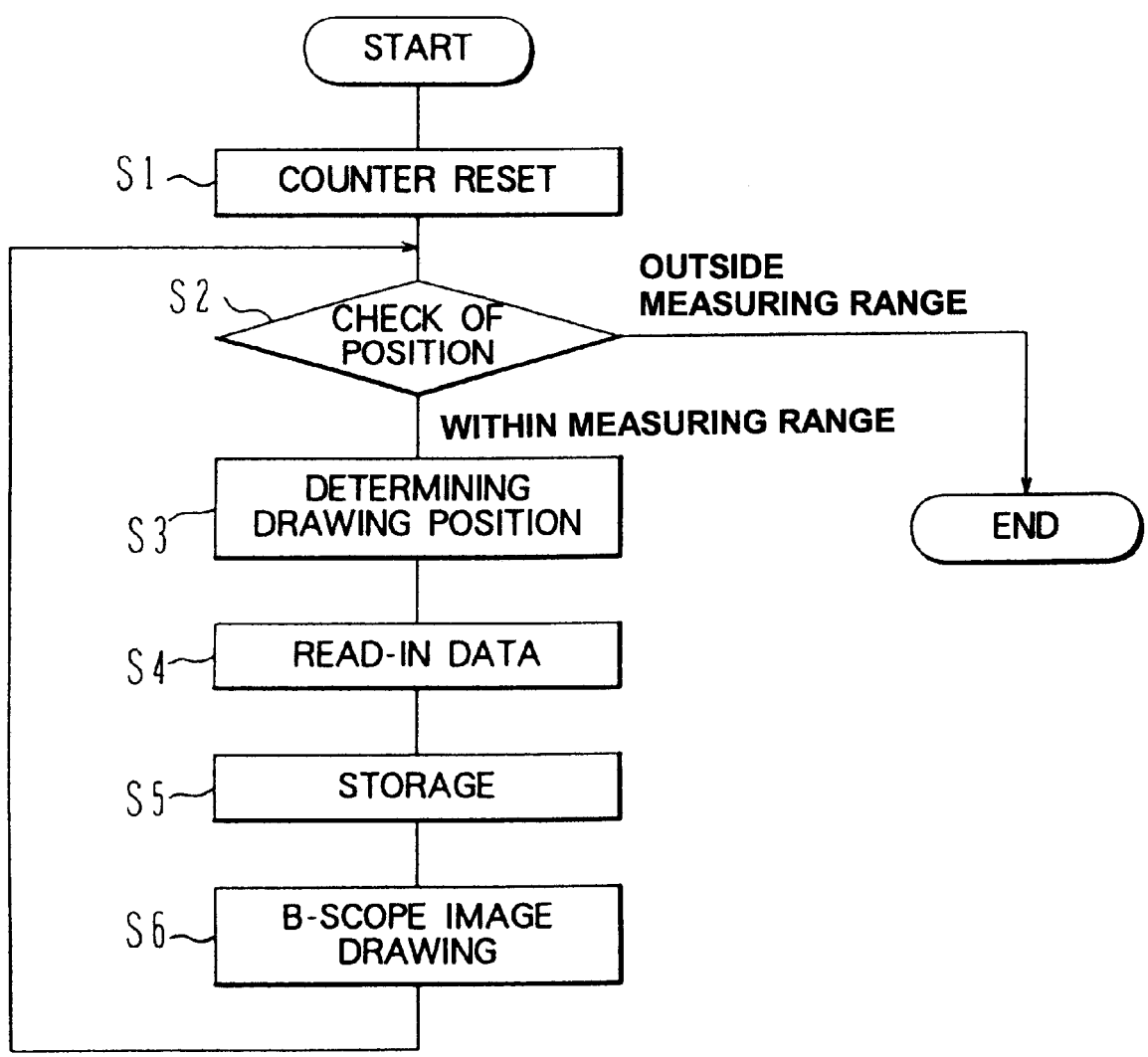
FIG. 5 is a flowchart showing an action of a storage-type B-scope image display in the first embodiment.

The display of B-scope images in accordance with the aforementioned B-scope image making program 42d is a sort of storage-type display. FIG. 5 shows a main part of the B-scope image making program 42d for executing the storage-type display. Next, the B-scope image display of storage-type will be explained with reference to the flow-chart shown in FIG. 5 and the illustrations shown in FIGS. 6A and 6B.

Figure 3:
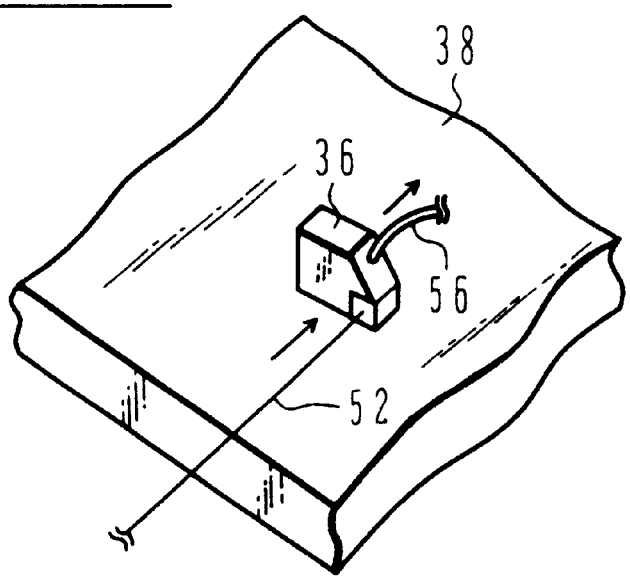
FIG. 3 is a diagram showing a state of scanning on an object to be inspected with an ultrasonic probe.
Figure 6A:
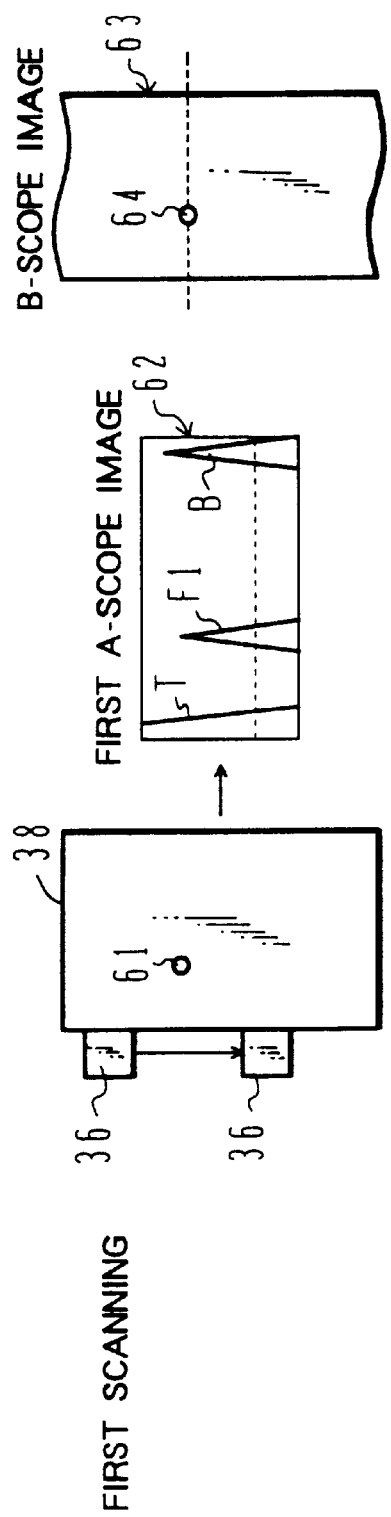
FIGS. 6A and 6B are diagrams illustrating the action of the storage-type B-scope image display in the first embodiment.
Figure 6B:
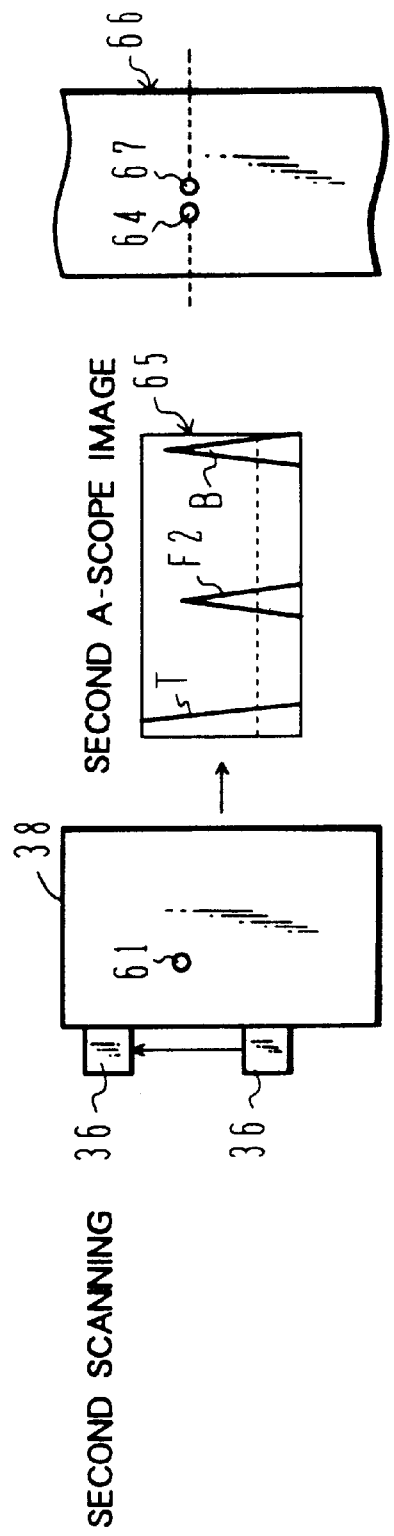

As shown in FIG. 3, a measuring range is determined on the inspected object and the probe 36 scans the measuring range. FIG. 6A shows a measuring action based on the first scanning (forward way), and FIG. 6B shows another measuring action based on the second scanning (backward way). In each of the two measuring actions the probe 36 measures the same spot in the object 38, that is, a defect 61. The first A-scope image (A-scope data) 62 and the first B-scope image 63 can be obtained through the first scanning action of probe 36. "F1" designates a waveform of the defect echo shown on the A-scope image 62, and 64 designates a defect image shown on the B-scope image 63. The second A-scope image (A-scope data) 65 and the second B-scope image 66 can be obtained through the second scanning action of the probe 36. "F2" designates a waveform of the defect echo shown on the A-scope image 65, and 67 designates a defect image shown on the B-scope image 66. On the B-scope image 66, the defect image 67, together with the aforementioned defect image 64, is shown. That is, when the probe 36 repeatedly scans the same spot on the object 38 in order to measure it, every time whenever the scanning action is carried out, the defect data (the peak-level of the defect echo waveform F2) is obtained and stored in the memory together with the last measured defect data (the peak-level of the defect echo waveform F1), and a subsequent defect image is shown on the B-scope image together with the last defect image. Namely, the display system in the ultrasonic detector of this embodiment has the configuration of a B-scope image display. This display system has a technical advantage such that it becomes easy to find out peak points on the B-scope image 66, for example, and thereby the defects can be detected with high accuracy.

The storage-type B-scope image display is executed according to the process shown in FIG. 5. The counter used for the encoder, which is included in the MPU 31, is reset in a step S1 in the first place. When moving the probe 36 on the object 38 to scan it, data of the moved amount (or position) of the probe 36 can be obtained. In a decision step S2, the position of the probe 36 on the object 38 is examined by use of the pulses outputted from the encoder 51. When the probe 36 exists outside of the measuring range, the measurement comes to an end. When the probe 36 exists within the measuring range, a drawing position is determined (a step S3). Here, the drawing position means a drawing line on the surface of the object, along which the probe 36 is moved to scan the object. Afterward, the measurement operator holds the probe 36 and moves it along the drawing line in a going and returning manner. Thus, the above-mentioned first and second scanning actions are carried out. The data on the echoes obtained through these scanning actions are digitized and stored in the aforementioned waveform memory 40 (a step S4). Peak data concerning the defect echoes obtained through the measurement due to respective scanning actions are stored respectively (a step S5). The stored peak data concerning the defect echoes, as illustrated in FIGS. 6A and 6B, are simultaneously drawn to show them on the display screen (a step S6). In accordance with the repetition of these steps the storage-type B-scope image display is carried out.

Although the example of easily displaying the B-scope images by use of the portable ultrasonic detector has been explained in the first embodiment, it is a matter of course to be able to apply the moved distance instrument with the encoder for other ultrasonic detectors of a different type.

Although in the first embodiment the probe 36 is the normal incidence probe, the angle probe for the angle beam method may be used. If the probe 36 is the angle probe, a C-scope image can be displayed. The display of the C-scope image is carried out by executing the aforementioned B-scope image making program 42d in regard to the combination of the A-scope data obtained through the normal measurement action and the moved distance data of the probe 36 obtained through the probe-moved-distance instrument to make images showing the inner state of the object. Hereinafter, the case of using the angle probe will be explained.

The second embodiment of the present invention will be explained in reference to FIGS. 7–11. In this second embodiment, the images showing the inner state of the object are displayed with the A-scope data obtained when carrying out the angle beam method.

In the second embodiment, components identical to those explained in the first embodiment are designated with the same reference numerals respectively and the explanations about them are omitted. The ultrasonic detector of the second embodiment and the signal processing in the ultrasonic detector are substantially identical to those in the first embodiment and the explanations thereof are also omitted.

Figure 7:
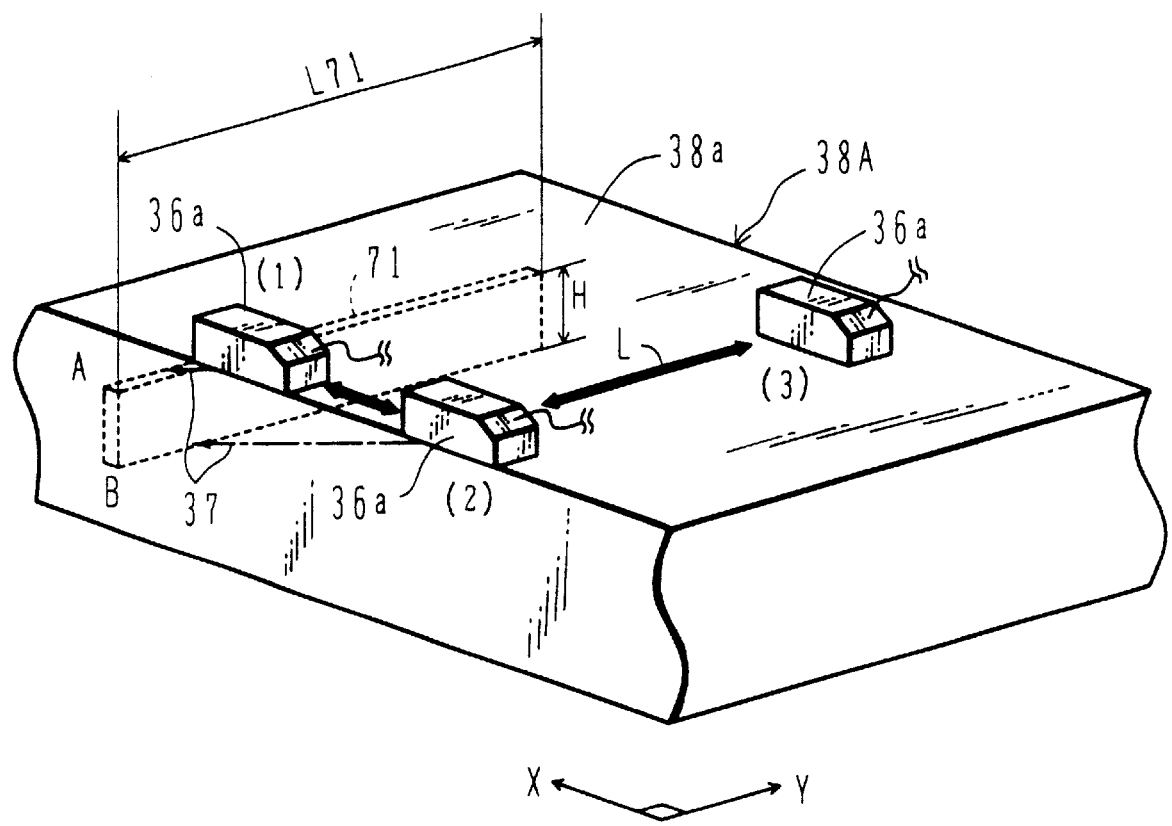
FIG. 7 is a perspective view showing an inspection state of the angle beam method in the second embodiment of the present invention.
Figure 8:
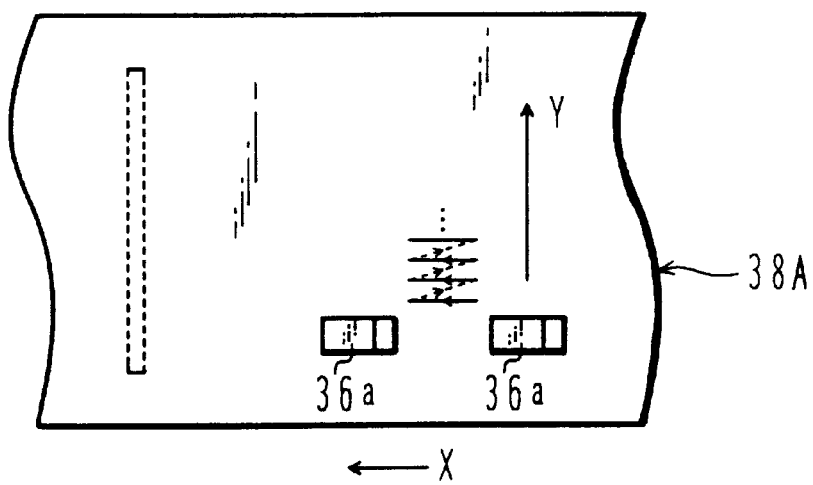
FIG. 8 is a plan view showing the inspection state of the angle beam method in the second embodiment.
Figure 9:
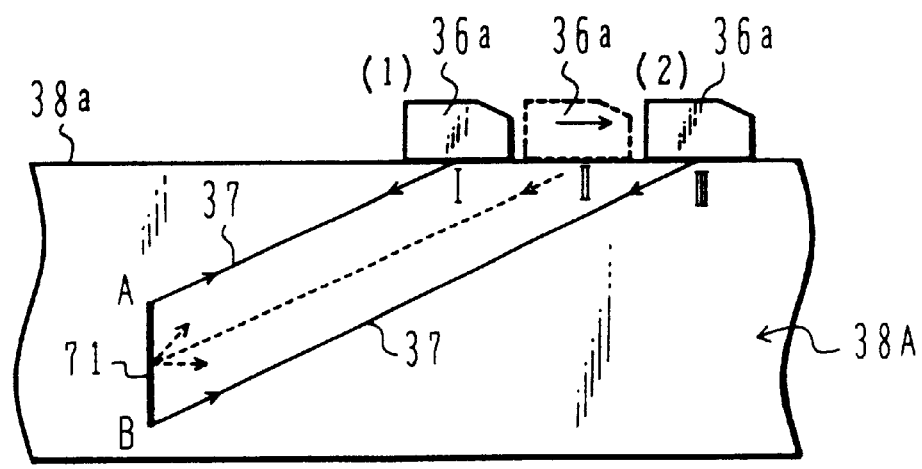
FIG. 9 is a longitudinal sectional view showing a scanning state on the object in the second embodiment.

As shown in FIG. 7, in this second embodiment, a defect 71 within the object 38A is detected by means of the ultrasonic probe 36a for the angle beam method. Further, in accordance with the angle beam method of the second embodiment, as shown in FIGS. 7–9, on an upper surface 38a, the ultrasonic probe 36a is moved toward a Y-direction to scan the object 38A (toward (3) with a distance L shown in FIG. 7), while it is repeatedly moved toward a X-direction substantially perpendicular to the position detectable direction of the ultrasonic probe 36a due to the encoder 51 with a short distance (between (1) and (2) shown in FIG. 7), and thereby the detected information on the reflected echo 37 and the position information provided from the encoder 51 are inputted into the device body 11 of the ultrasonic detector 10. Data on the reflected echo 37, which is included within a predetermined gate range, is stored in the waveform memory 40 through the input/output control circuit 32 and the A/D converter 39. The width of the gate in the second embodiment is set to become relatively wide.

Figure 10:
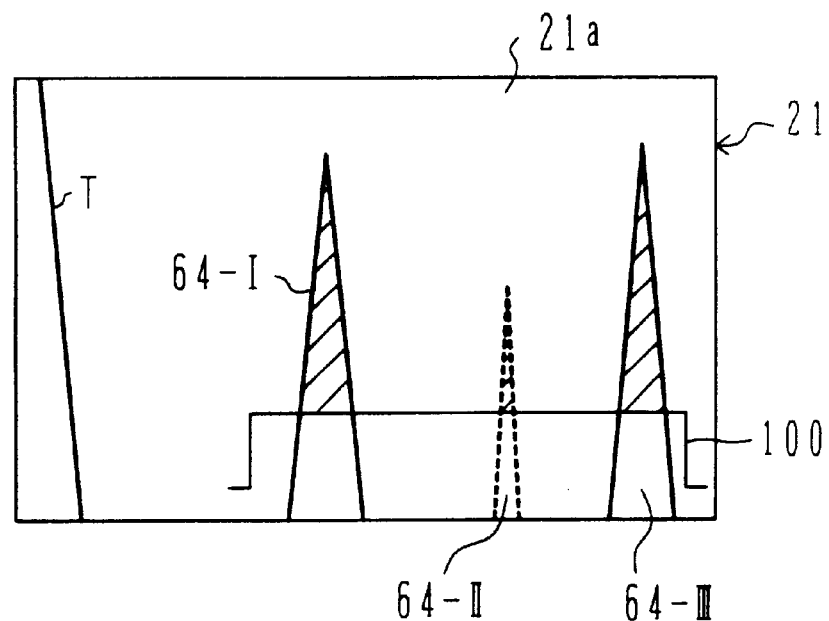
FIG. 10 is a diagram showing a correspondence relationship between A-scope data obtained in the second embodiment and a gate signal.
Figure 11:
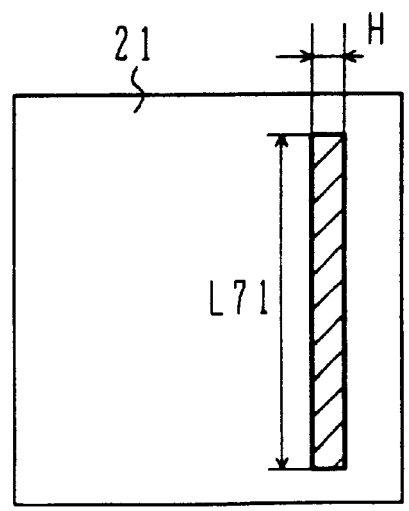
FIG. 11 is a diagram showing one example of the image obtained by processing the A-scope data in the second embodiment.
Figure 12:
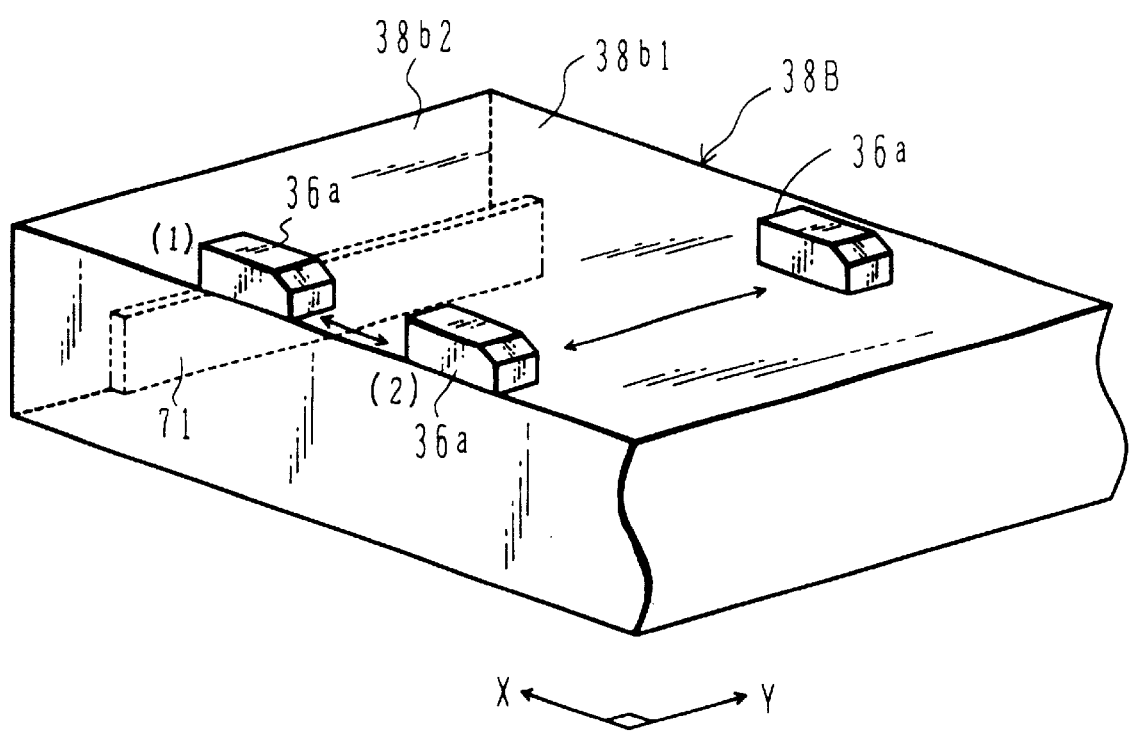
FIG. 12 is a perspective view showing the inspection state of the angle beam method in the third embodiment.

In the structure of the second embodiment as mentioned above, when the defect 71 has a length in a depth direction, a distance of propagation path for the ultrasonic wave is changed in response to the X-direction movement of the probe 36a as shown in the respective states I, II, III of FIG. 9, for example. That is, the propagation path of the state I is comparatively short, and the propagation path of the state II is longer than that of the state I, and further the propagation path of the state III becomes longest, and therefore the times necessary for the propagation of the reflected echo 37 from the defect 71 to the ultrasonic probe in the respective states I, II and III are different with one another. Consequently, when detecting the echoes as the A-scope data, as shown in FIG. 10, signal positions corresponding to the defect 71 respectively at the positions of the ultrasonic probe 36a in the states I, II and III are different mutually. Namely, the reflected echo 37 from the defect 71 is detected as a signal 64-I when the ultrasonic probe 36a is positioned at the spot indicated by the state I, and further at the spots indicated by the states II and III it is detected as signals 64-II and 64-III respectively. In the second embodiment, as shown in FIG. 10, the width of a gate 100 is set to be comparatively long so as to be able to detect respective reflected echo signals 64-I, 64-II and 64-III, and further all of the signals whose amplitude level is larger than the threshold value set on the gate 100 (regions shown by diagonal lines in FIG. 10) are stored in the waveform memory 40 in a manner so that the signals correspond to the position information provided by the encoder 51. Here, the movement of the probe 36a for the scanning action in the X-direction is very small as mentioned above, and therefore outputted values of the encoder 51 at the spots of the states I, II and III are substantial equal. Consequently, when making an image of the defect 71 by use of the A-scope data stored in the waveform memory 40, as shown in FIG. 11, the lateral length of the image is the depth H of the defect 71 and the longitudinal length thereof is the length L71 of the defect 71. Accordingly, the ultrasonic detector of the second embodiment can detect the position of the defect 71 based on the A-scope data obtained through the angle beam method, and in addition can detect shape information on the depth and length of the defect 71 exactly.

Next, the third embodiment of the present invention will be explained in reference to FIGS. 12–16.

The third embodiment is different from the second embodiment in a respect that an object 38B to be inspected has an end surface 38b2 in the vicinity of the measuring part and a reflected echo signal due to the end surface 38b2 is also stored in the waveform memory 40. In addition, the Y-direction scanning action of the ultrasonic probe 36a is carried out to be substantially parallel to the end surface 38b2 on an upper surface 38b1. The other components of the third embodiment are basically identical to those of the second embodiment.

Figure 13:
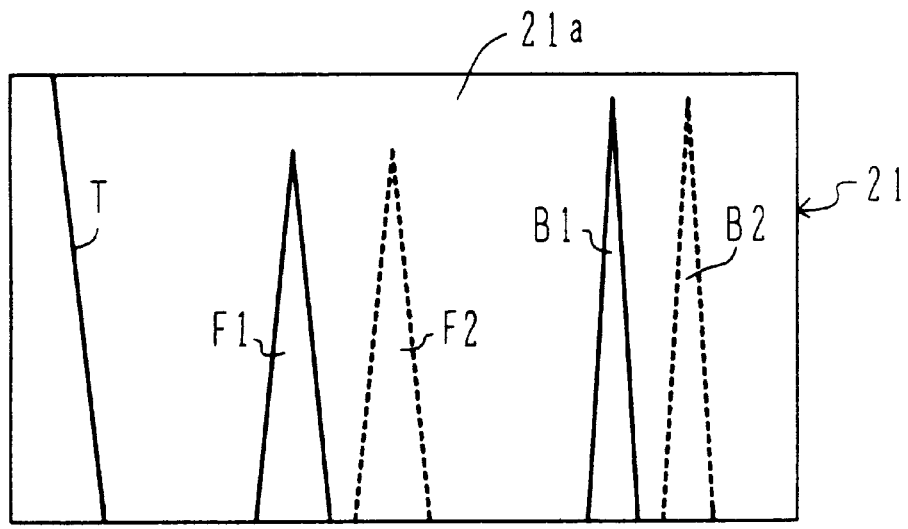
FIG. 13 is a diagram showing one example of A-scope image in the third embodiment.
Figure 14:
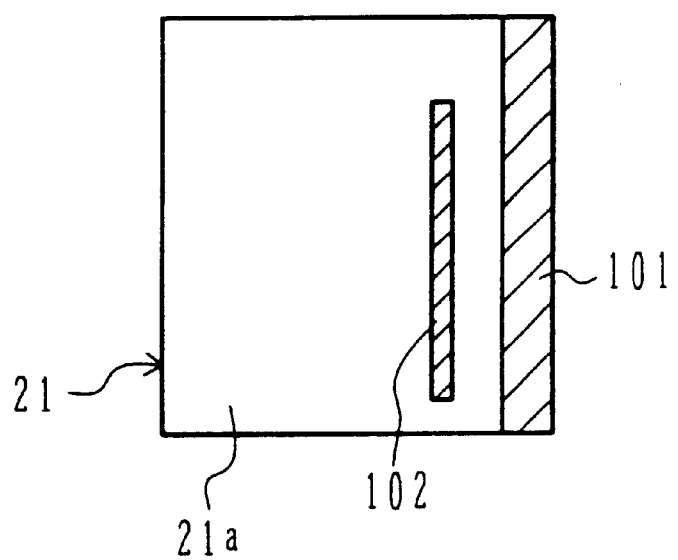
FIG. 14 is a diagram showing one example of the image obtained by processing the A-scope data in the third embodiment.

In the third embodiment with the structure mentioned above, as shown in FIG. 13, the reflected echo signals F1 and F2 due to the defect 71 and the reflected echo signals B1 and B2 are detected on the basis of the short movement of the probe 36a for the X-direction scanning action. In the third embodiment, further, the width of the gate 100 is set to be longer than the gate width in the second embodiment so that the reflected echo signals from the end surface 38b2 can be also stored in the waveform memory 40. Therefore, when making images by use of data stored in the waveform memory 40, as shown in FIG. 14, a part 101 corresponding to the reflected echoes from the end surface 38b2 and a part 102 corresponding to the reflected echoes from the defect 71 are displayed on the screen 21a of the display section 21. In FIG. 13, F1 and B1 designate the reflected echo signals from the defect 71 and the end surface 38b2 respectively when the ultrasonic probe 36a exists at the spot of (1), F2 and B2 designate the reflected echo signal from the defect 71 and the reflected echo signal from the end surface 38b2 respectively when the ultrasonic probe 36a exists at the spot of (2), and T designates a signal showing an echo reflected on the surface of the object when transmitting the ultrasonic wave to the object.

Figure 15:
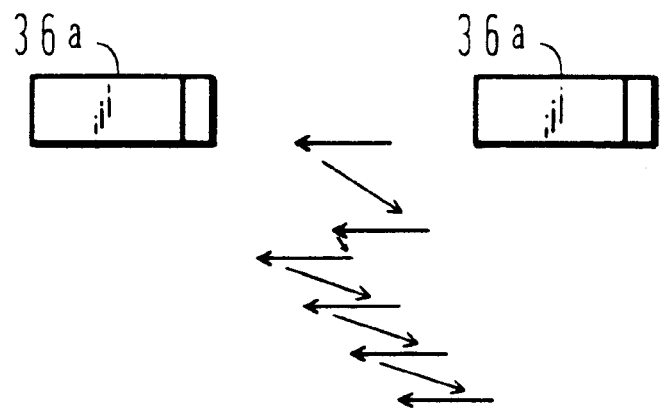
FIG. 15 is a diagram showing an undesirable scanning example in the angle beam method.
Figure 16:
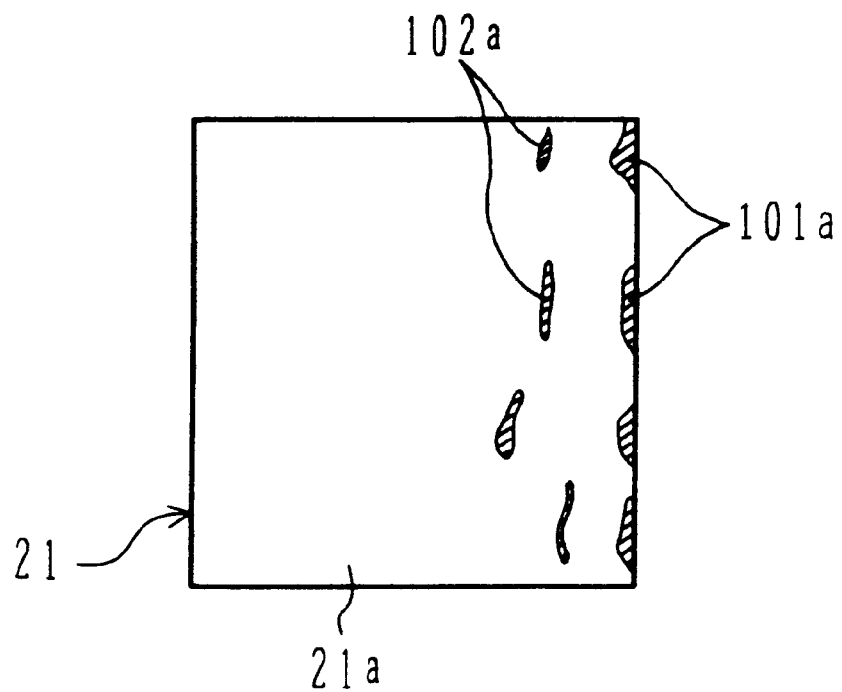
FIG. 16 is a diagram showing one example of image obtained by performing the undesirable scanning in the angle beam method.

By the way, in the portable ultrasonic detector 10 mentioned above, the scanning direction and the scanning position of the ultrasonic probe 36a are changeable in practice, since the probe 36a is manually operated. When the scanning action of the probe 36a is remarkably changed in the X-direction as shown in FIG. 15, for example, the reflected echo signals based on the defect 71 and the end surface 38b2 are also changeable in response to the movement of the probe 36a. When displaying the images on the display screen as a matter of course, images 101a and 102a respectively corresponding to the end surface 38b2 and defect 71 are both remarkably different from their actual images as shown in FIG. 16. Here, as to the end surface 38b2, its shape is originally clear based on the appearance and therefore it will be quite obvious whether the result shown in FIG. 16 is accurate or not. Accordingly, in relation to the judgement on the image of the end surface, the judgement on propriety of the defect data can be done. Thus, the end surface 38b2 is used as a standard surface (or a standard part) in the inspected object, which relates to a means for contributing to evaluate the propriety of the manual scanning action, and the image of the standard section is displayed, together with the image of the defect to be originally inspected, on the screen of the display section.

The ultrasonic detection of the third embodiment has the technical effect such that to make images based on the reflected echo data concerning the end surface 38b2 enables the measurement operator to easily judge whether the data obtained by means of the angle beam method is proper or not, together with the technical effects of the aforementioned second embodiment. Specifically, it becomes possible to easily judge whether the manual scanning action of the angle probe by the measurement operator was proper or not.

Although the number of the gates is one in the aforementioned embodiments, it is not limited to one. For example, a plurality of gates, the number of which is equal to two or more than two, may be prepared by use of software. When the number of the gates is two, one gate is set to retrieve the signal due to the standard surface while the other gate is set to retrieve the signal due to the defect. The level of respective gates is determined in response to the retrieved signal.

As mentioned above, according to the present invention, since the portable ultrasonic detector is provided with the moved distance instrument realized by use of the encoder, it is possible in the ultrasonic detector to display the inner scope images such as the B-scope image and the images based on the angle beam method with the simple system configuration, to easily obtain the defect echo waveforms, and further to improve detection accuracy of the defect position.

Further, the present invention can heighten the detection accuracy of the defect position by making the image based on the data obtained through the angle beam method, and further, in case of measuring the object with the standard surface, it is easy to judge whether the data obtained through the angle beam method is proper or not, by setting the width of the gate signal so that it can include the reflected echo signal due to the standard surface.

What is claimed is:

1. A portable ultrasonic detector comprising:
   a moved distance instrument comprised of an encoder for detecting a moved amount and a counting section for counting the moved amount based on a detection signal outputted from said encoder;
   a movable wire incorporated within said encoder, wherein the detection signal outputted from said encoder is determined by a moved amount of said movable wire;
   an ultrasonic probe connected to a tip of said movable wire;
   an ultrasonic wave inspecting section for producing A-scope data when scanning an inspected object with said ultrasonic probe; and
   an arithmetic processing section that receives moved distance data of said ultrasonic probe that is measured by said moved distance instrument, said processing section including means for generating images by combining the A-scope data with the moved distance data;
   wherein, while repeatedly scanning the same spot of said object with said ultrasonic probe, peaks of defect echo waves generated in every scan are stored in groups in a memory and at least two peaks of defects are indicated as the generated image.

2. The portable ultrasonic detector according to claim 1, further comprising display means, wherein in a picture displayed on said display means one axis indicates the moved distance of said ultrasonic probe and another axis indicates function of time.

3. The portable ultrasonic detector according to claim 1, wherein the A-scope data stored in said memory is based on reflected echo signals detected within a predetermined gate signal.

4. The portable ultrasonic detector according to claim 3, wherein the number of the gate signal is one.

5. The portable ultrasonic detector according to claim 3, wherein the number of the gate signal is two.

6. The portable ultrasonic detector according to claim 3, wherein said object has a standard surface and the gate signal is set to have a width capable of including the reflected echo signals due to the standard surface.

7. The portable ultrasonic detector according to claim 1, wherein said ultrasonic probe is manually moved for a scanning action.

8. The portable ultrasonic detector according to claim 7, wherein said object has a standard part and an image of said standard part is included in the generated image.

9. A portable ultrasonic detector comprising:
an ultrasonic probe used for ultrasonic scanning by an angle beam method, which is moved manually;
display means for displaying an object to be inspected by use of ultrasonic signals obtained from said ultrasonic probe when manually scanning the object with said ultrasonic probe;
only one encoder for detecting a moved amount of said ultrasonic probe, which encoder is used to detect movement in a scanning direction perpendicular to an ultrasonic wave emission direction;
a moved distance instrument including the encoder that detects an amount of movement of the ultrasonic probe and which comprises a counting section for counting the moved amount based on a detection signal outputted from said encoder; and
an arithmetic processing section for generating images of the object on the basis of A-scope data obtained when manually scanning the object plural times at different positions with respect to a defect with said ultrasonic probe and a signal indicating the moved amount of said ultrasonic probe outputted from said moved distance instrument during each scanning at said different positions;
wherein said arithmetic processing section stores a plurality of A-scope data in groups in a memory, which are obtained during scanning with said ultrasonic probe at a direction substantially perpendicular to another direction along which said ultrasonic probe is moved to detect its position by said encoder, and said display means displays images showing the scanned object on the basis of the data stored in said memory.

10. The portable ultrasonic detector according to claim 9, wherein in a picture displayed on said display means one axis indicates the moved distance of said ultrasonic probe and another axis indicates function of time.

11. The portable ultrasonic detector according to claim 9, wherein the A-scope data stored in said memory is based on reflected echo signals detected within a predetermined gate signal.

12. The portable ultrasonic detector according to claim 11, wherein the number of the gate signal is one.

13. The portable ultrasonic detector according to claim 11, wherein the number of the gate signal is two.

14. The portable ultrasonic detector according to claim 11, wherein said object has a standard surface and the gate signal has a width that includes the reflected echo signals due to a standard surface in the object.

15. The portable ultrasonic detector according to claim 9, wherein said object has a standard part, and said scanned object image that is displayed includes an image of said standard part.

\* \* \* \* \*